(12) United States Patent
Piaget et al.

(10) Patent No.: US 7,744,542 B2
(45) Date of Patent: Jun. 29, 2010

(54) IMPLANTED AIR PASSAGE SENSORS

(75) Inventors: Thomas Piaget, Minneapolis, MN (US);
Paul Huelskamp, St. Paul, MN (US);
Jeffrey E. Stahmann, Ramsey, MN
(US); John D. Hatlestad, Maplewood,
MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1025 days.

(21) Appl. No.: 11/379,396

(22) Filed: Apr. 20, 2006

(65) Prior Publication Data

US 2007/0249950 A1    Oct. 25, 2007

(51) Int. Cl.
*A61B 5/0205* (2006.01)
(52) U.S. Cl. ......................... 600/529; 600/301; 600/486
(58) Field of Classification Search ................. 600/529, 600/538, 537, 309, 341, 300, 311, 489, 301, 600/486; 607/20, 42
See application file for complete search history.

(56) References Cited

U.S. PATENT DOCUMENTS

| | | | |
|---|---|---|---|
| 5,047,350 | A | 9/1991 | Switalski et al. |
| 5,564,434 | A | 10/1996 | Halperin et al. |
| 5,876,353 | A | 3/1999 | Riff |
| 6,024,704 | A * | 2/2000 | Meador et al. ............ 600/486 |
| 6,076,015 | A | 6/2000 | Hartley et al. |
| 6,109,113 | A | 8/2000 | Chavan et al. |
| 6,132,384 | A | 10/2000 | Christopherson et al. |
| 6,140,740 | A | 10/2000 | Porat et al. |
| 6,152,885 | A * | 11/2000 | Taepke ..................... 600/561 |
| 6,198,965 | B1 | 3/2001 | Penner et al. |
| 6,234,973 | B1 * | 5/2001 | Meador et al. ............ 600/486 |
| 6,237,398 | B1 | 5/2001 | Porat et al. |
| 6,239,724 | B1 | 5/2001 | Doron et al. |
| 6,266,564 | B1 * | 7/2001 | Hill et al. ................... 607/9 |
| 6,277,078 | B1 | 8/2001 | Porat et al. |
| 6,431,175 | B1 | 8/2002 | Penner et al. |
| 6,432,050 | B1 | 8/2002 | Porat et al. |
| 6,438,238 | B1 | 8/2002 | Callahan |

(Continued)

FOREIGN PATENT DOCUMENTS

EP    0702977 A2    3/1996

(Continued)

OTHER PUBLICATIONS

"U.S. Appl. No. 11/276,466, Response filed Aug. 16, 2007 to Restriction Requirement mailed Jul. 20, 2007", 10 pgs.

(Continued)

*Primary Examiner*—Patricia C Mallari
*Assistant Examiner*—Michael D'Angelo
(74) *Attorney, Agent, or Firm*—Schwegman, Lundberg & Woessner, P.A.

(57) ABSTRACT

A physiological sensor is located within the airway of the subject's body, such as for measuring barometric pressure and communicating this value to a blood pressure or other monitoring device, which can derive gauge pressure using the barometric pressure and a measured absolute pressure within the body. The physiological sensor may also detect one or more other physiological parameters such as air flow, sound, or a chemical property. It may be anchored within the airway with the ability to communicate wirelessly to one or more other medical devices, such as an implanted cardiac function management device. Methods of use are also described.

19 Claims, 7 Drawing Sheets

U.S. PATENT DOCUMENTS

| | | | |
|---|---|---|---|
| 6,438,408 | B1 | 8/2002 | Mulligan et al. |
| 6,442,413 | B1 | 8/2002 | Silver |
| 6,475,170 | B1 | 11/2002 | Doron et al. |
| 6,486,588 | B2 | 11/2002 | Doron et al. |
| 6,504,286 | B1 | 1/2003 | Porat et al. |
| 6,622,049 | B2 | 9/2003 | Penner et al. |
| 6,628,989 | B1 | 9/2003 | Penner et al. |
| 6,629,951 | B2 | 10/2003 | Laufer et al. |
| 6,643,548 | B1 | 11/2003 | Mai et al. |
| 6,664,111 | B2 | 12/2003 | Bentsen et al. |
| 6,666,826 | B2 | 12/2003 | Salo et al. |
| 6,699,186 | B1 | 3/2004 | Wolinsky et al. |
| 6,713,828 | B1 | 3/2004 | Chavan et al. |
| 6,720,709 | B2 | 4/2004 | Porat et al. |
| 6,743,173 | B2 | 6/2004 | Penner et al. |
| 6,764,446 | B2 | 7/2004 | Wolinsky et al. |
| 6,840,956 | B1 | 1/2005 | Wolinsky et al. |
| 6,926,670 | B2 | 8/2005 | Rich et al. |
| 6,949,075 | B2 | 9/2005 | Hatlestad et al. |
| 6,968,743 | B2 | 11/2005 | Rich et al. |
| 6,970,742 | B2 | 11/2005 | Mann et al. |
| 7,035,684 | B2 | 4/2006 | Lee |
| 7,115,096 | B2 | 10/2006 | Siejko et al. |
| 7,123,962 | B2 | 10/2006 | Siejko et al. |
| 2001/0026111 | A1 | 10/2001 | Doron et al. |
| 2002/0045921 | A1 | 4/2002 | Wolinsky et al. |
| 2002/0077673 | A1 | 6/2002 | Penner et al. |
| 2002/0098120 | A1 | 7/2002 | Blazewicz et al. |
| 2002/0177782 | A1 | 11/2002 | Penner et al. |
| 2002/0188323 | A1 | 12/2002 | Penner et al. |
| 2003/0023181 | A1 | 1/2003 | Mault |
| 2003/0032892 | A1 | 2/2003 | Erlach et al. |
| 2003/0139787 | A1 | 7/2003 | Eggers |
| 2003/0191392 | A1 | 10/2003 | Haldeman et al. |
| 2004/0032187 | A1 | 2/2004 | Penner et al. |
| 2004/0044393 | A1 | 3/2004 | Yarden et al. |
| 2004/0077937 | A1 | 4/2004 | Yarden |
| 2004/0127792 | A1 | 7/2004 | Siejko et al. |
| 2004/0134496 | A1* | 7/2004 | Cho et al. ............ 128/204.23 |
| 2004/0138568 | A1 | 7/2004 | Lo et al. |
| 2004/0172083 | A1 | 9/2004 | Penner |
| 2004/0204744 | A1 | 10/2004 | Penner et al. |
| 2005/0154321 | A1 | 7/2005 | Wolinsky et al. |
| 2005/0182342 | A1* | 8/2005 | Dinsmoor et al. ........... 600/593 |
| 2005/0288722 | A1* | 12/2005 | Eigler et al. .................. 607/9 |
| 2006/0037617 | A1* | 2/2006 | Walke et al. ........... 128/207.15 |
| 2006/0064134 | A1* | 3/2006 | Mazar et al. .................. 607/17 |
| 2006/0215862 | A1 | 9/2006 | Huynh et al. |
| 2006/0282000 | A1 | 12/2006 | Zhang et al. |
| 2007/0049977 | A1 | 3/2007 | Von Arx et al. |
| 2007/0142727 | A1* | 6/2007 | Zhang et al. ................ 600/486 |
| 2007/0208390 | A1 | 9/2007 | Von Arx et al. |
| 2008/0058885 | A1 | 3/2008 | Belalcazar et al. |

FOREIGN PATENT DOCUMENTS

| WO | WO-99/55223 A1 | 11/1999 |
|---|---|---|
| WO | WO-99/55225 A1 | 11/1999 |

OTHER PUBLICATIONS

"U.S. Appl. No. 11/276,466, Restriction Requirement mailed Jul. 20, 2007", 6 pgs.

"U.S. Appl. No. 11/276,466, Amendmnet and Response filed Jan. 9, 2009 to Final Office Action mailed Oct. 7, 2008", 11 pgs.

"U.S. Appl. No. 11/276,466, Response filed Jan. 25, 2008 to Non-Final Office Action mailed Sep. 25, 2007", 14 pgs.

"U.S. Appl. No. 11/276,466, Non-Final Office Action mailed Sep. 25, 2007", 10 pgs.

"U.S. Appl. No. 11/276,466, Final Office Action mailed Oct. 7, 2008", 10 pgs.

"U.S. Appl. No. 11/276,466, Non-Final Office Action mailed Mar. 4, 2009", 10 pgs.

"U.S. Appl. No. 11/469,018, Non-Final Office Action mailed Feb. 5, 2009", 7 pgs.

"Laryngeal and Tracheal Stents", [online]. [retrieved Feb. 6, 2006]. Retrieved from the Internet: <URL: http://www.tracheostomy.com/surgery/stents.htm>, © 1996-2005), 3 pgs.

"Oxygen Sensor—General description", [online]. (c) 2004 Sensors for Medicine and Science, Inc. [retrieved Feb. 22, 2006]. Retrieved from the Internet: <URL: http://www.s4ms.com/oxygen_general.htm>, (May 19, 2004), 4 pgs.

"Venula Pictures", *CTS Net—The Cardiothoracic Surgery Network*, [online]. [retrieved Feb. 6, 2006]. Retrieved from the Internet: <URL: http://www.ctsnet.org/graphics/experts/Thoracic/venuta/venuta_lg_14.jpg>, 1 pg.

"VTI Technologies—Products and Applications", [online]. [retrieved Feb. 22, 2006]. Retrieved from the Internet: <URL: http://www.vti.fi/productsen/productsen_4_1_1_1.html>, (2005), 2 pgs.

Hauck, R. W., et al., "Implantation of Accuflex and Strecker stents in malignant bronchial stenoses by flexible bronchoscopy", *Chest*, 112(1), (Jul. 1997), 134-44.

McClay, J. E., "Laryngeal & Tracheal Stents", [online]. [retrieved Feb. 6, 2006]. Retrieved from the Internet: <URL: http://www.emedicine.com/ent/topic593.htm#target2>, (Aug. 18, 2004), 25 pgs.

McNamee, J. E., et al., "Peribronchial electrical admittance measures lung edema and congestion in the dog", *J Appl Physiol.*, 49(2), (Aug. 1980), 337-341.

Piaget, T., et al., "Implanted Air Passage Sensors", U.S. Appl. No. 11/379,396, filed Apr. 20, 2006, 28 pgs.

Takahata, K., et al., "Stentenna: a micromachined antenna stent for wireless monitoring of implantable microsensors", *The 25th Annual International Conference of the IEEE Engineering in Medicine and Biology Society* (EMBS 2003), vol. 4, (Sep. 2003), 3360-3363.

Venuta, F., et al., "Airway Stenting", [online]. Retrieved from the Internet: <URL: http://www.ctsnet.org/sections/clinicalresources/thoracic/venuta.html>, *CTS Net—The Cardiothoracic Surgery Network*, © 1998-2006), 11 pgs.

"U.S. Appl. No. 11/276,466, Final Office Action mailed Aug. 7, 2009", 14 pgs.

"U.S. Appl. No. 11/276,466, Pre-Appeal Brief Request filed Nov. 9, 2009", 5 pgs.

"U.S. Appl. No. 11/276,466, Response filed Jun. 4, 2009 to Non Final Office Action mailed Mar. 4, 2009", 16 pgs.

"U.S. Appl. No. 11/469,018, Final Office Action mailed Oct. 16, 2009", 8 pgs.

"U.S. Appl. No. 11/469,018, Response filed Jun. 5, 2009 to Non Final Office Action mailed Feb. 5, 2009", 11 pgs.

"U.S. Appl. No. 11/469,018, Response filed Nov. 12, 2009 to Final Office Action mailed Oct. 16, 2009", 13 pgs.

\* cited by examiner

IMPLANTED AIR PASSAGE SENSORS

TECHNICAL FIELD

This patent document pertains generally to implantable medical devices, and more particularly, but not by way of limitation, to an implantable air passage sensor.

BACKGROUND

Physiological conditions of a subject can provide useful information about the subject's health status, such as to a physician or other caregiver. Devices may be implanted within a patient's body for monitoring certain physiological conditions. For example, a vascularly implantable pressure sensor can be used to measure blood pressure, however, the resulting measurement provides only an absolute pressure value of the immediate anatomical environment, which does not take into account ambient barometric pressure external to the body. Such a vascularly implantable pressure sensor is typically not capable of communicating gauge pressure because it is isolated from the ambient pressure external to the body.

SUMMARY

Exposing an implantable sensor to an ambient external environment can provide additional information not available within the body. This document describes, among other things, certain examples in which a physiological sensor is implanted within the airway of the subject's body, such as for measuring barometric pressure, for example. In such an example, the measured barometric pressure can be communicated to a monitoring device, such as a separate implantable medical device, for example. The implantable medical device can derive gauge pressure using this barometric pressure information together with an absolute pressure measured within the body. The physiological sensor may additionally or alternatively detect one or more other physiological parameters, such as air flow, physiological sounds, or chemical properties. The physiological sensor may be anchored within a person's airway and may be able to communicate wirelessly to one or more other implantable or other medical devices.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
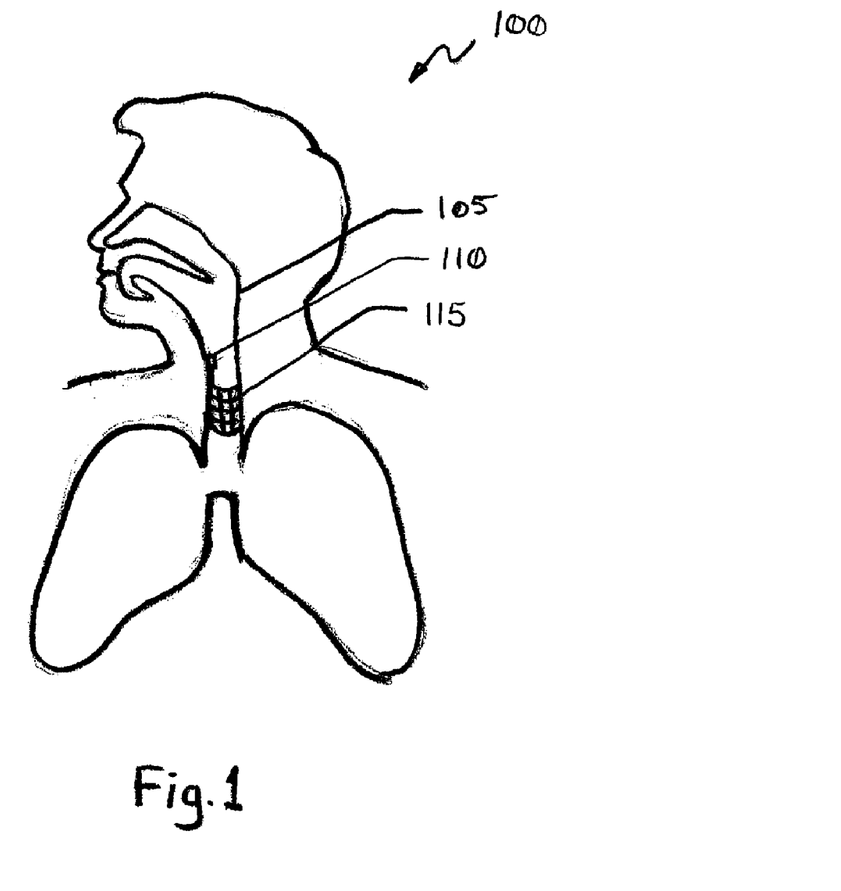
FIG. 1 illustrates a particular example of a sensor within the human respiratory system.

FIG. 1 illustrates generally, by way of example, but not by way of limitation, one example of portions of a system 100 to detect at least one physiological or external parameter, such as barometric pressure, within the airway 105 of the human respiratory system. In the present example, the system includes a sensor 110 to detect a physiological parameter or external parameter from within the body. The sensor 110 is shown in the example of FIG. 1 as attached to an anchor 115, which is disposed within an airway 105, such as a trachea, or other similar region of the respiratory system. In this example, the system 100 comprises the sensor 110 and anchor 115 as a self-contained unit. However, one or more other medical devices, either internal or external, may also be included in the system 100, and used such as to communicate with the sensor 110.

In certain examples, the airway sensor 110 includes a pressure sensor, such as to detect barometric pressure. One suitable example of a pressure sensor is described in U.S. Pat. No. 6,666,826, issued Dec. 23, 2003 to Salo et al. and assigned to Cardiac Pacemakers, Inc., which is incorporated herein by reference in its entirety, including its description of an example of a pressure sensor. Salo describes a pressure transducer comprising micro-electrical-mechanical systems (MEMS) technology, which uses semiconductor or like fabrication techniques to build microscopic mechanical devices in silicon or other materials. The pressure transducer using this technology can include a micro-machined capacitive or piezoresistive transducer, for example. In certain examples, the pressure transducer used to measure pressure may include resistive strain gauge technology.

While a system including an implantable barometric pressure sensor that is communicatively coupled to an implantable medical device is specifically discussed below as an illustrative example, the present systems and methods are not so limited. For example, sensor 110 can be used with one or more non-implantable sensors that sense one or more physiological signals, such as those indicative of the circulatory blood volume of a person and barometric pressure detection. In certain examples, physiological parameters to be monitored include acute symptoms, chronic symptoms, or a combination of both. In various examples, the sensor 110, is implemented by hardware, software, or a combination of hardware and software. In certain examples, the sensor 110 can detect a physiological or external parameter such as pressure, flow, or gas concentration. The sensor 110 can also include accompanying signal processing or other circuits, such as an application-specific or a general-purpose circuit, such as a microprocessor or a portion thereof, a microcontroller or portions thereof, and a programmable logic circuit or a portion thereof.

Figure 2:
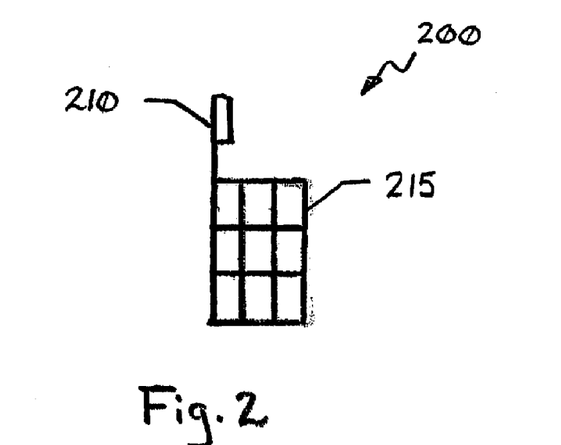
FIG. 2 shows one example of a sensor and anchor as shown in FIG. 1.

FIG. 2 illustrates an example in which a sensor and anchor assembly 200 may be implanted within the trachea, bronchi, or elsewhere within the airway of the subject's body. The assembly 200 includes a sensor module 210 attached to an anchor mechanism 215. In certain examples, the anchor mechanism 215 comprises an expandable mesh material. In certain examples, the sensor module 210 is welded to the inner surface of a metal anchor mechanism 215. In certain examples, the anchor mechanism 215 is formed of an expandable silicone material, with the sensor module 210 attached to or encapsulated within a wall of the anchor mechanism 215. An expandable silicone stent may be used to treat a patient with dyspnea, which includes as a symptom a sensation of having shortness of breath due to obstructed airway. In certain applications, a silicone stent is preferred over expandable metallic mesh, due to the ability of silicone to prevent tissue growth through the stent.

Locating the sensor module 210 within a tracheal stent permits chronic endotracheal sensing. The sensor module 210 may include one or more sensors capable of detecting one or more physiological parameters. In certain examples, the sensor module 210 is able to detect an airway pressure such as a barometric pressure, an inspiratory pressure, or an expiratory pressure. In certain examples, the sensor module 210 is able to detect temperature, such as by using a thermocouple or thermistor. In certain examples, the sensor module 210 is able to detect airway flow, such as inspiratory flow, expiratory flow, minute ventilation (a measure of air volume over time) or tidal volume (a measure of the amount of air inhaled or exhaled per breath). In certain examples, measuring flow includes using a piezo crystal used to generate a set frequency and to receive a resulting measured frequency, and to use a Doppler shift to determine flow information.

In certain examples, the sensor module 210 detects a presence or concentration of an airway gas, such as $O_2$ (oxygen) or $CO_2$ (carbon dioxide), for example. Such information can be used, for example, to estimate the subject's oxygen consumption, which, in turn, can be used to infer the subject's activity level, for example. In certain examples, the sensor module 210 comprises a low power fluorescent oxygen sensor, such as a miniature light emitting diode (LED) which is typically coated with a fluorescing substance that responds to oxygen exposure. This produces a signal indicative of nearby oxygen concentration. In certain examples, the sensor module 210 comprises a non-dispersive infrared (IR) diode, which is typically coated with a material that responds to $CO_2$, thereby producing a signal indicative of nearby carbon dioxide concentration.

Figure 9:
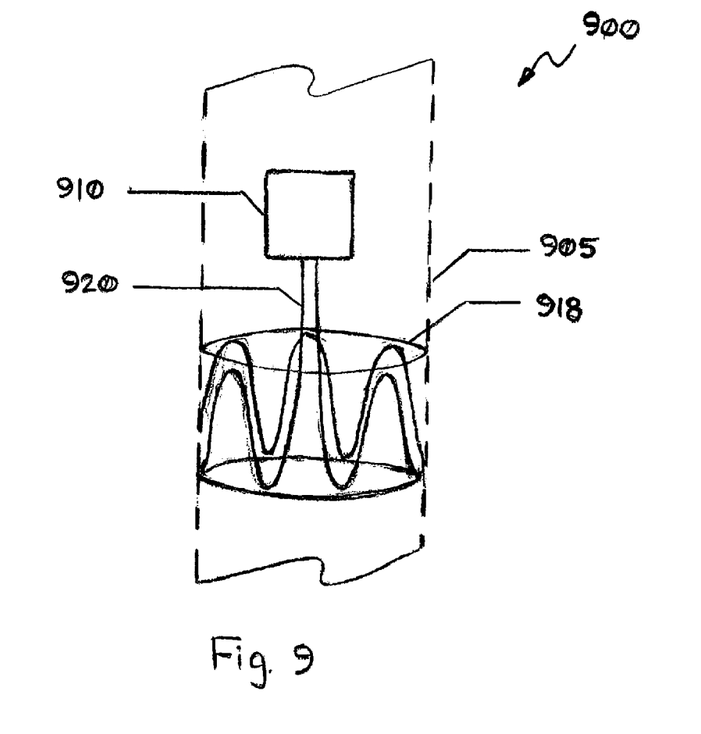
FIG. 9 illustrates an example of a sensor anchored to a flexible alloy strut.

In certain examples, the sensor module 210 is sensitive to an airway dimension, such as a bronchial diameter. FIG. 9 illustrates an example in which a sensor module 910 and anchor assembly 900 reside within the trachea or bronchi 905, such as against the walls of the trachea or bronchi. In this example, the sensor module 910 is connected by an insulated anchor wire 920 to a flexible metal alloy strut 918, such as a nitinol alloy strut 918. In this example, the strut 918 can act as an inductor, such that the proximity of the individual coils of anchor wire 920 change a self-inductance measured by the sensor module 910. In certain examples, as the diameter of the trachea or bronchia 905 decreases, the anchor wire 920 is squeezed closer together. This increases self-inductance. In certain examples, an initial bronchial diameter is measured at the time of implant of a sensor module 910, which is programmed to estimate bronchial diameter based upon measured intra-bronchial pressures.

Figures 11A, 11B:
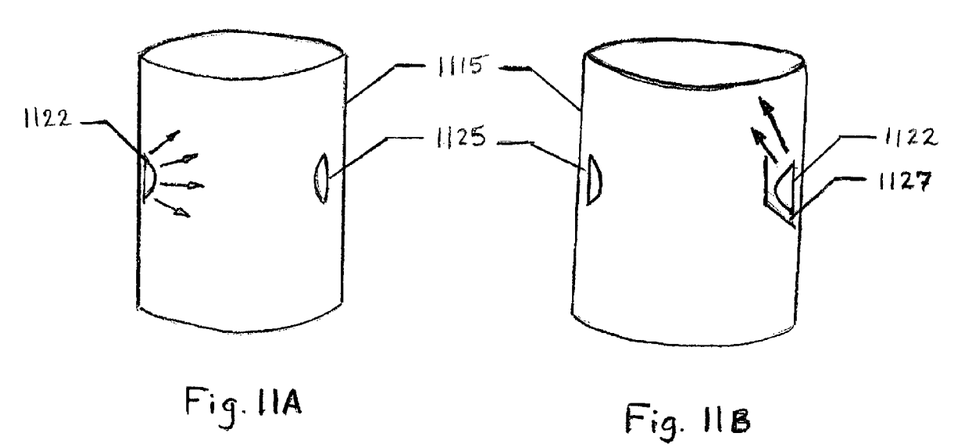
FIG. 11A-B illustrate anchor systems for detecting particulate concentration.

In certain examples, the sensor module 210 is able to detect the presence or concentration of one or more particulates in the airway, such as smoke (ash), pollen, or dust. FIGS. 11A and B illustrate two examples of an anchor mechanism 1115 for this purpose. FIG. 11A illustrates a 'bright field' technique in which a light source 1122 (visible, ultraviolet (UV) or other) is attached to or embedded within a wall of the anchor mechanism 1115 and directed to illuminate the airway within an interior lumen of the anchor mechanism 1115. A photodetector 1125 is directed toward the light source 1122. The photodetector 1125 produces a signal that is responsive to the intensity of the light source 1122. Airway particulates, such as inhaled particles, will obstruct or occlude the light traveling from the light source 1122 to the photodetector 1125, and this change is measurable from the signal produced by the photodetector 1125. In certain examples, a 'dark field' technique of FIG. 11B may be used. In such examples, a photodetector 1125 within the anchor mechanism 1115 produces a signal indicative of the light within the airway. A light source 1122 is shielded by a deflector 1127 which will only allow indirect light to travel within the airway. The photodetector 1125 of FIG. 11A is therefore more sensitive to light than in the example of FIG. 11B. In the "dark field" technique, light reflected from particles in the airway is detected by the photodetector 1125, which produces a signal indicative of this reflected light. The bright field example of FIG. 11A is typically well-suited for detection of opaque particulates (dust, smoke, etc.), and the dark field example of FIG. 11B is typically well-suited for transparent or reflective particulates (moisture or other saturated gases that scatter light).

In the example of FIG. 2, the anchor mechanism 215 typically includes a stent-like arrangement in which the sensor module 210 and anchor mechanism 215 can be passively fixed at the desired implant site, such as the airway 105. In passive fixation arrangements, the anchor 215 is typically held in place using a self-contained force or pressure, such as a self-expanding (or manually-expanded) stent that is compressed during implanting and positioning, and that is allowed to expand at the point of anchor, thereby remaining fixed preferably without piercing the adjacent tissue. In certain examples, the fixation mechanism alternatively comprises a cork-shaped (e.g., non-uniform diameter cylindrical) device to allow the system 200 to be anchored within the airway 105, such as within a branch from the bronchi.

Figure 10:
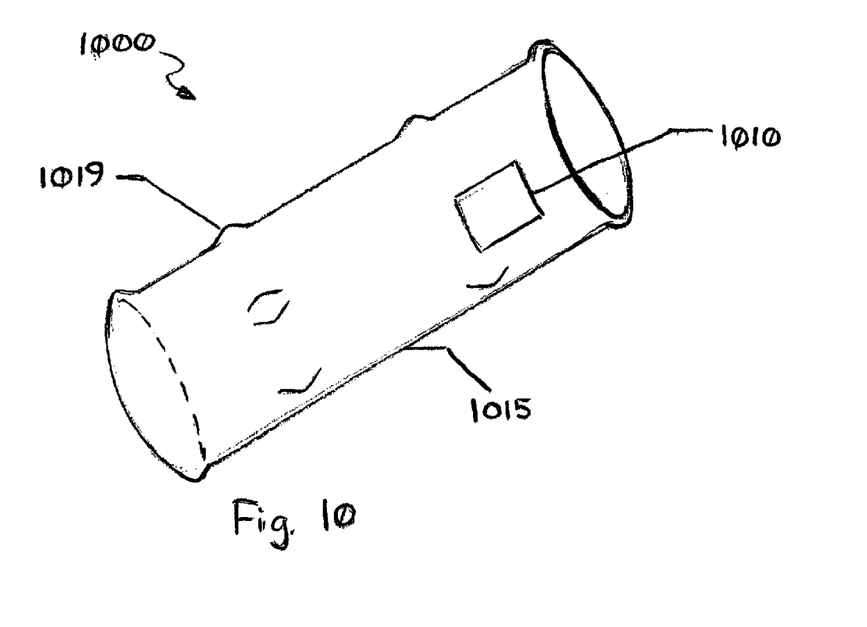
FIG. 10 shows one example of a sensor and anchor assembly formed of expandable silicone material.

FIG. 10 illustrates an example of a sensor and anchor assembly 1000 having a fixation anchor mechanism 1015 formed of an expandable silicone material having extensions 1019 which allow passive fixation of the anchor assembly 1000 within the implant site. The sensor module 1010 may either be attached to or encapsulated within the wall of the anchor mechanism 1015.

Alternatively, active fixation may be employed. This may include, but by no means are limited to, a screw-like or harpoon-like fixation mechanism designed to pierce the surrounding tissue. In either arrangement, the surrounding tissue typically eventually covers the anchor and helps hold it at the implant site. Alternatively, in certain examples, the anchor may serve the additional purpose of maintaining patency of the airway and it may be preferred that the tissue be inhibited from covering the anchor.

Figure 3:
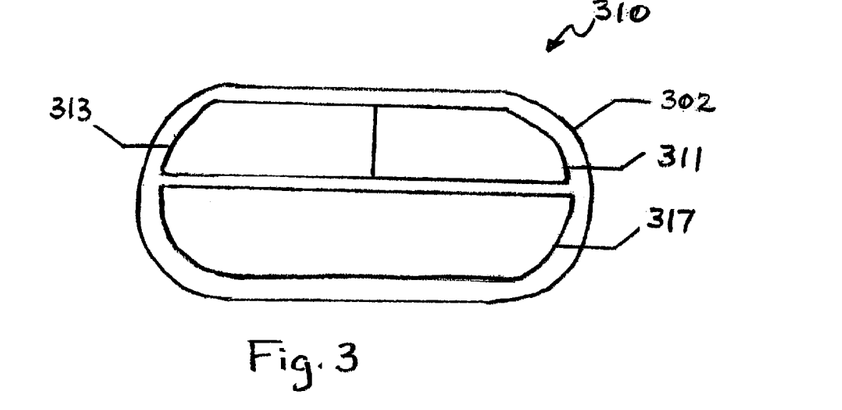
FIG. 3 illustrates one example of a sensor having a detector, a communication module and an energy source.

FIG. 3 illustrates an example in which the sensor module 310 comprises a sealed housing 302 configured to enclose at least a portion of one or more of the components that make up the sensor module 310. The material for the housing 302 typically includes a flexible or rigid biocompatible material that will withstand conditions of long-term exposure inside a body. In certain examples, the sensor module 310 includes a detector 313 used to detect one or more physiological parameters. A communication module 311 allows the detector 313 to interface with another device, such as a separate detector or circuit located within the same housing 302, or alternatively located remotely from the implant site of sensor 310, either at a location within the body, or at a location external to the body. In certain examples, the communication module 311 includes a processor for processing the detected parameter signal into an electrical signal indicative of the parameter for derivation of further information such as determination of the gauge pressure. In certain examples, an energy source 317 provides power, such as to both the detector 313 and the communication module 311. In certain examples, the energy source 317 may be wirelessly rechargeable, such as by transcutaneous inductive power transmission, for example.

In certain examples, the communication module 311 comprises an inductor to communicate via modulation of a mutual inductance, for example. In certain examples, the communication module 311 includes signal processing circuitry corresponding to the physiological or external parameter for processing a corresponding electrical signal representative of the parameter of interest. In certain examples, the communication module 311 is configured to transmit information wirelessly by use of acoustic or ultrasonic energy, inductive transmission, or radio frequency (RF) communication. The communication module 311 may transmit information from the sensor module 310 to another location within the body, which need not be adjacent the sensor module 310, but instead can be remote from the sensor module 310. In such an example, the sensor module 310 may provide information used by a remotely implanted medical device as an input to control delivery of energy or therapy to the subject. In certain examples, the communication module 311 is configured to use the subject's body as an electrical signal conductor to transmit information wirelessly. In certain examples, the communication module 311 transmits information wirelessly to a location outside the subject's body.

Figure 4:
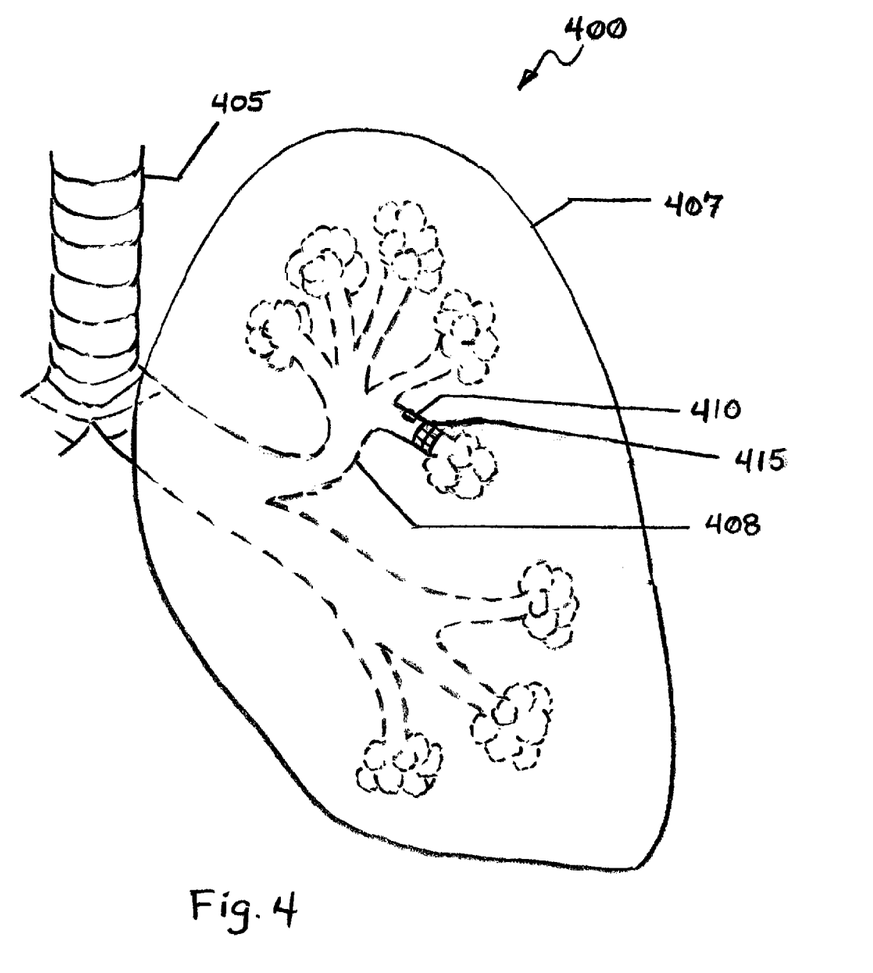
FIG. 4 illustrates an example of a sensor anchored in the bronchi airway of a human lung.

FIG. 4 shows an example of a system 400 comprising a sensor module 410 attached to an anchor 415, which in certain examples is located within a bronchial branch 408 of a subject's lung 407. This provides an alternative to anchoring within the trachea 405. In certain examples, wireless communication by the sensor module 410 may use the anchor 415 as an antenna, such as to improve signal strength for transmission or sensitivity to reception.

Figure 5:
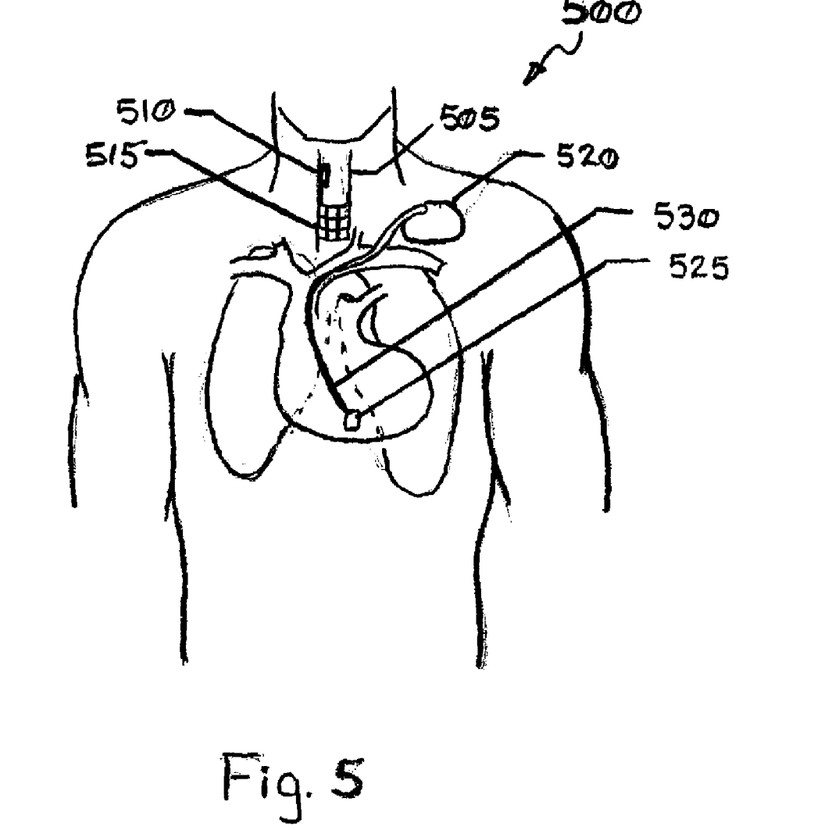
FIG. 5 illustrates an example of a sensor anchored in the trachea and an implantable medical device within the circulatory system.

FIG. 5 illustrates an example of a system 500 including a first implantable medical device comprising a first sensor module 510 attached to an anchor 515 and implanted within a trachea 505. A second implantable medical device (for example, an implantable cardiac function management device) comprises a communication module 520 and a second sensor 525. In the example of FIG. 5, the second sensor 525 is typically communicatively connected to an electronics unit, such as by one or more wires 530, for example, by an intravascular lead. Although the communication module 520 is shown as being attached to the second sensor 525 by one or more wires 530, wireless communication could similarly be used. In certain examples, the first sensor module 510 senses a barometric pressure and the second sensor 525 senses absolute (blood) pressure, such as from a location within a pulmonary artery.

In certain examples, the communication module 520 communicates with the first sensor 510 and includes processing circuitry to derive gauge pressure. Gauge pressure can be computed as: $P_g = P_a - P_b$; where $P_g$ is the gauge pressure, $P_a$ is the absolute pressure (e.g., measured within the body) and $P_b$ is the barometric pressure (e.g., measured by an airway sensor with access to the external barometric pressure). Certain measured physiological signals derived from the circulatory system are affected by ambient conditions that are not detectable using absolute pressure alone. For example, a change in elevation that is accompanied by a change in ambient air pressure may be misinterpreted by an implanted cardiac function management device that does not compute gauge pressure as a change in absolute blood pressure. This may cause the implanted cardiac function management device to erroneously adjust therapy delivery if it uses absolute blood pressure as a control input for delivering such therapy. However, the ability to determine gauge pressure reduces or eliminates such errors, thereby allowing the implanted cardiac function management device to maintain appropriate therapy.

In certain examples, the sensor module 510 includes a processor to receive information about a measured physiological parameter from the second sensor 525, and to provide a responsive indication of one or more physiological events, such as cardiac arrhythmia (which may include heart rate sensing), cardiac ischemia (reduced blood flow and oxygen sensing), hypertension (high blood pressure sensing), sleep-disordered breathing or Cheyne-Stokes respiration (abnormal breathing characterized by alternating periods of shallow and deep breathing, which may include air flow sensing), chronic obstructive pulmonary disease (such as bronchitis or emphysema, which may include air flow sensing), asthma or respiratory congestion, or pulmonary edema (which may include fluid accumulation sensing).

In certain examples, cardiac arrhythmia events may be determined from the processor receiving physiological signals from an intrinsic electrical or other heart rate sensor. In certain examples, an internally detected electrocardiogram (ECG or EKG) may be used to identify elevation or depression of the ST Segment (the ST segment represents the period from the end of ventricular depolarization to the beginning of ventricular repolarization), such as for detecting a myocardial infarction resulting in cardiac ischemia. Cardiac ischemia may also be determined from the processor receiving one or more physiological signals from a blood flow sensor and identifying a change (reduction) in blood flow as an indication of possible narrowed or blocked coronary vessels. In certain examples, hypertension events may be determined from the processor receiving one or more physiological signals from a blood pressure sensor and identifying a change (increase) in pressure.

In certain examples, sleep-disordered breathing, Cheyne-Stokes respiration, or chronic obstructive pulmonary disease (COPD) events may be determined from the processor receiving physiological signals from a tracheal or other air flow sensor and identifying a disturbance in breathing rhythm or breathing volume. In certain examples, sleep-disordered breathing may include apnea (e.g., no respiration for a period of 10 seconds or more) or hypoapnea (e.g., tidal volume reduction of 30% or more for a period of 10 seconds or more). Tidal volume represents the amount of air inhaled and exhaled in a breath. Cheyne Stokes respiration involves a recurrent and typically periodic amplitude modulation of tidal volume. In certain examples, the above-mentioned indications may be detected using a transthoracic impedance sensor. Other indications that may be detected using the transthoracic impedance sensor include asthma, respiratory congestion, or pulmonary edema events. Pulmonary edema can be determined by a change in total thoracic impedance, which includes a near-DC component. In certain examples, the indication may occur from the processor receiving physiological signals from a fluid sensor and identifying a change (increase) in fluid concentration in the lungs as an indication of pulmonary edema risk or the onset of asthma symptoms from mucus secretions and inflammation. In certain examples, chronic obstructive pulmonary disease (COPD) and asthma can be indicated by a change in the respiration/expiration ratio such as reduced maximal expiratory flow and low forced expiratory volume.

Figure 6:
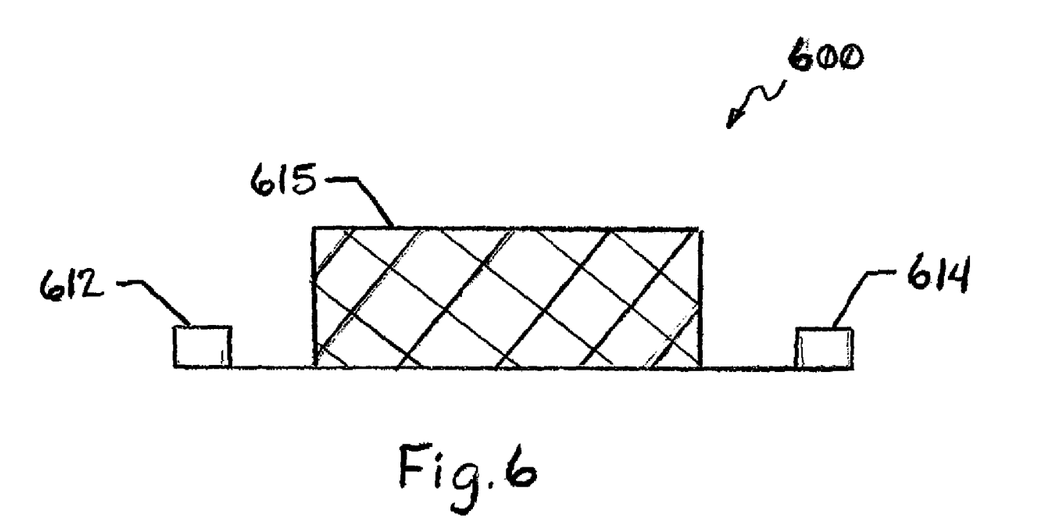
FIG. 6 shows one example of two sensors attached to an anchor similar to that illustrated in FIG. 2.

FIG. 6 illustrates an example of a system 600 having multiple pressure sensors 612 and 614, such as to detect air flow using the pressure difference observed between the two sensors 612 and 614. The system 600 in FIG. 6 is similar to system 200 shown in FIG. 2, but having multiple sensors 612 and 614. In certain examples, both sensors 612 and 614 are attached to anchor 615. This provides a known fixed distance between the two sensors 612 and 614, which is helpful in deriving flow. In certain examples, anchor 615 provides an electrical conductor or other communication conduit to transmit information between the two sensors 612 and 614, or between one or more of the sensors 612 and 614 and a signal processing circuit, power source, or communication circuit.

Figure 7:
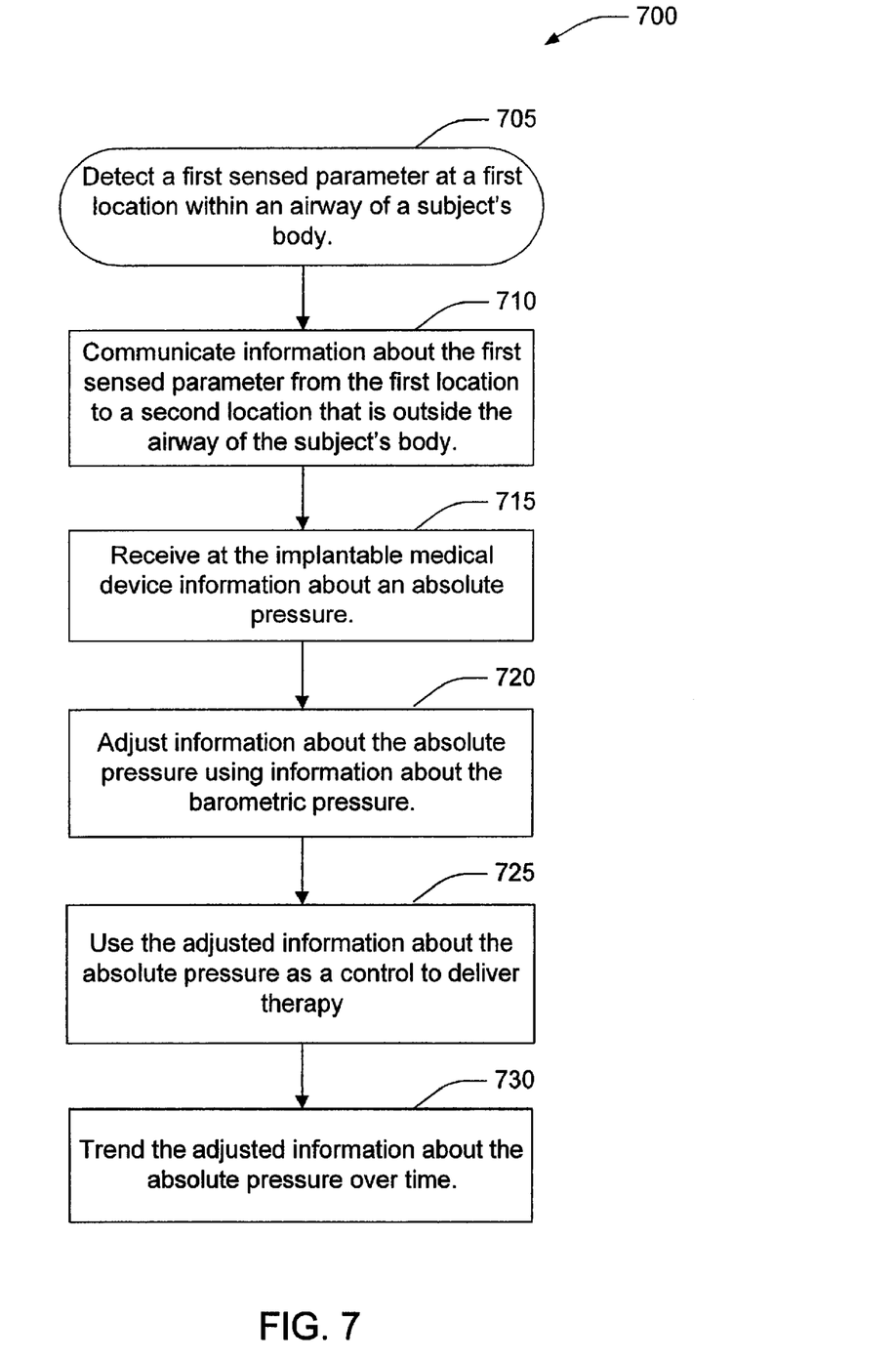
FIG. 7 is a is a flow diagram of an example of a method of detecting physiological parameters utilizing a sensor similar to that illustrated in FIG. 1 and FIG. 2 and using derived information.

FIG. 7 shows a flow diagram 700 illustrating an example of a method of sensing one or more physiological parameters within the airway of a subject's body. At 705, a first sensed parameter is detected at a first location within an airway of a subject's body. Examples of such parameters include a barometric pressure, a physiologic sound, or a physiological chemical property. At 710, information about the first sensed parameter is communicated from the first location to a second location that is outside the airway of the subject's body, such as by direct conductive connection or by wireless transmission. In certain examples, the wireless communication includes using an acoustic signal, a radio frequency signal, an ultrasound signal, an inductive signal, or electrical signal communication using the body as an electrical signal conductor. The anchor may be used as an antenna for receiving or transmitting information, as discussed above, or a separate antenna may be provided. In certain examples, at 715, information about an absolute pressure is received at the second location (such as by implanted cardiac function management or other implanted medical device at the second location, for example). In certain examples, at 720, information about the absolute pressure is adjusted, such as by using received information about the barometric pressure, such as to obtain a gauge pressure. In certain examples, at 725, the adjusted information about the absolute pressure is used as a control for delivering therapy. In certain examples, at 730, the adjusted information about the absolute pressure is used as a diagnostic, for example, it can be trended over time, such as to monitor changing conditions, or to control therapy.

Figure 8:
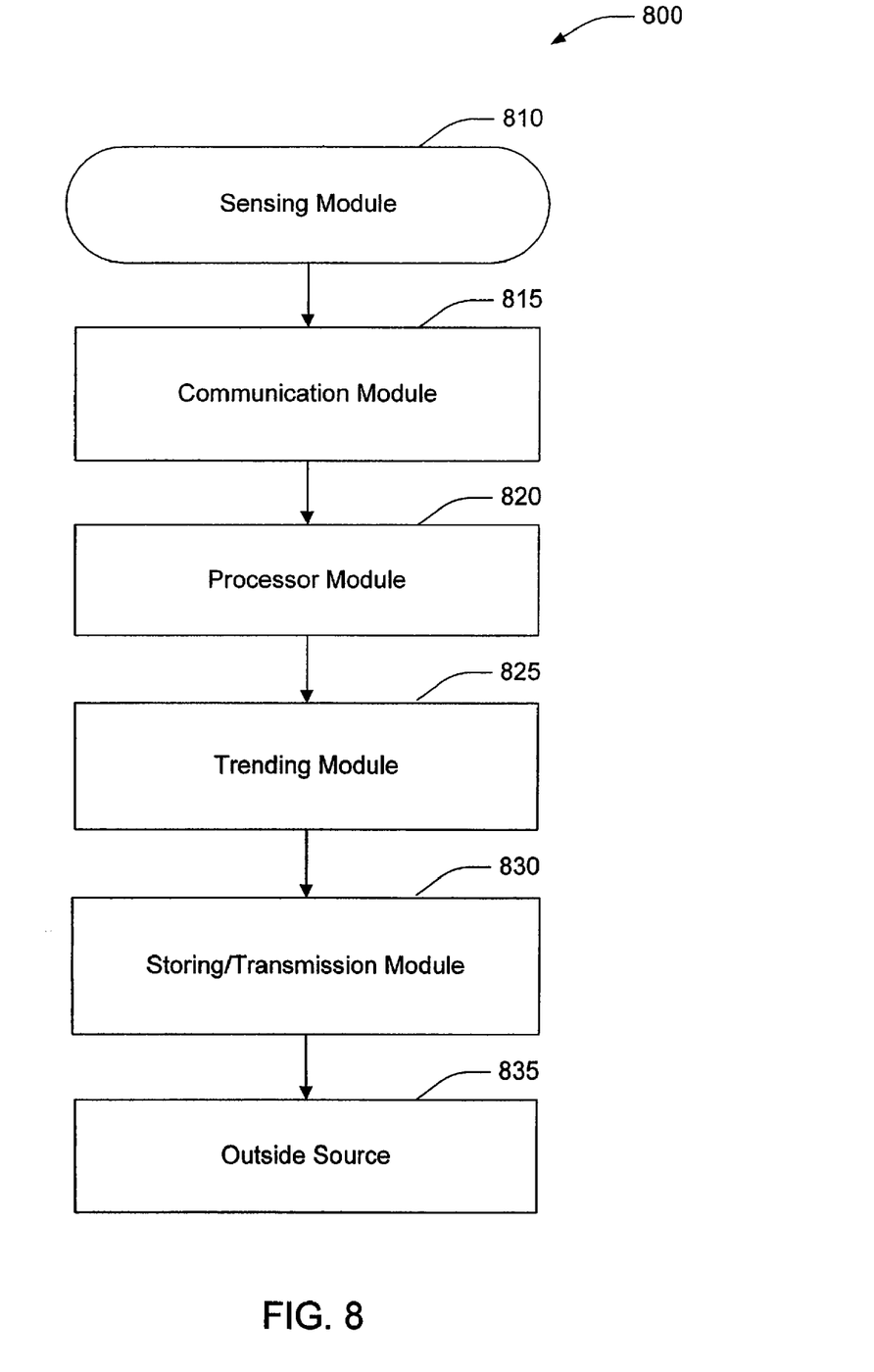
FIG. 8 illustrates an example of a system for trending a physiological parameter.

FIG. 8 illustrates a system or device 800 for trending a physiological parameter. System 800 may include a sensing module 810 for detecting a physiological parameter, a communication module 815 for providing signal interface between the sensing module 810 and the processor module 820, a processor module 820 for analyzing and storing data, and a trending module 825 for a variety of functions. The trending module 825 may collect parameter values, trend collected parameter values over set time intervals, compare trends at different times, transfer data to an outside source, average parameter values over time, and compare trended data to perform analysis or report for a caregiver. Trend data may be collected in a storage/transmission module 830 and subsequently transferred to an outside source 835 such as an advanced patient management system that may be associated with system or device 800.

The trending of data in the trending module 825 may be generally used to track or monitor characteristic activities anticipated from trend data which may be useful in diagnosis for physicians. In certain examples, the trending module 825 collects oxygen level and respiration rate over time which is stored for later collection by the physician. The data may be organized or displayed for the physician in a table or graphical format. In certain examples the data may be averaged, or derived into a single number or value. The parameter values and method of collection can be determined by the physician to provide an overview of the patient well-being. Trend data may be used to monitor the progress of patient conditions or the effect of one or more drugs or therapy being applied to the subject.

It is to be understood that the above description is intended to be illustrative, and not restrictive. For example, the above-described embodiments (or aspects thereof) may be used in combination with each other. Other embodiments will be apparent to those of skill in the art upon reviewing the above description. For example, thoracic sensing can be used. These include, but are by no means limited to thoracic motion (e.g., due to respiration, heart beat or body movement), thoracic posture (e.g., due to upper body prone or bent with respect to lower body), thoracic pressure, thoracic sounds such as the lungs (e.g., crackle, cough, wheeze or rates) or the heart (e.g., first through fourth heart sounds, referred to as S1, S2, S3 or S4, or murmurs), thoracic voltage (thorax voltage such as heart electrocardiogram or muscle electromyogram) or transthoracic impedance (thorax impedance measurement). An example of transthoracic impedance sensing is described in U.S. Pat. No. 6,076,015 to Hartley et al., which issued Jun. 13, 2000, and which is assigned to Cardiac Pacemakers, Inc., and which is incorporated by reference herein in its entirety, including its description of a transthoracic impedance sensor and signal processing. Hartley et al. describes a transthoracic impedance as measuring impedance across the chest or thorax, which provides, among other things, respiratory or ventilation information of the subject.

The scope of the invention should, therefore, be determined with reference to the appended claims. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A system comprising:
    an implantable medical device;
    a first sensor module separate from and unattached to the implantable medical device, at least a portion of which is adapted to reside within an airway of a subject's body, wherein the first sensor module comprises:
        a first detector configured to detect an external air pressure;
        a communication module, coupled to the first detector, the communication module configured to transmit information about the external air pressure to the implantable medical device; and
        an energy storage device, coupled to at least one of the first detector and the communication module; and
        an anchor, attached to the first sensor module, the anchor configured to fixate at least a portion of the first sensor module within the airway; and
    an absolute physiological pressure sensor module, at least a portion of which is adapted to reside within a circulatory system of the body, wherein the absolute physiological pressure sensor module comprises:
        an absolute physiological pressure detector configured to detect an absolute pressure;
        a communication module, coupled to the absolute physiological pressure detector, configured to transmit information about the absolute pressure to the implantable medical device;
        an energy storage device, coupled to at least one of the absolute physiological pressure detector and communication module; and
        an anchor configured to fixate at least a portion of the absolute physiological pressure detector within the circulatory system; and
    wherein the implantable medical device includes a communication module configured to receive information about the external air pressure from the communication module of the first sensor module and information about the absolute pressure from the communication module of the absolute physiological pressure sensor module, the implantable medical device including a processor configured to derive a gauge pressure using the external air pressure and the absolute pressure.

2. The system of claim 1, including a processor to receive information about the external air pressure and the absolute pressure and to provide a responsive indication of hypertension.

3. The system of claim 1,
    wherein the communication module of the implantable medical device is configured to wirelessly receive information about the external air pressure from the communication module of the first sensor module.

4. The system of claim 3,
    wherein the implantable medical device is separate from and unattached to the absolute physiological pressure sensor module.

5. The system of claim 1, in which the anchor includes an expandable stent-like structure configured to maintain airway patency.

6. The system of claim 1, in which the anchor includes an antenna.

7. The system of claim 1, in which the communication module of the first sensor module comprises an inductor for communication.

8. The system of claim 1, in which the communication module of the first sensor module is configured to transmit information wirelessly, and comprises one or more of an ultrasonic transmitter, an inductive transmitter, and a radio frequency (RF) transmitter.

9. A method comprising:
    detecting a barometric pressure from an at least partially implantable first sensor at a first location within an airway of a subject's body;
    detecting an absolute pressure from an at least partially implantable second sensor at a second location within a circulatory system of the subject's body;
    communicating information about the barometric pressure and information about the absolute pressure to an implantable medical device at a third location within the subject's body;
    deriving information about a gauge pressure from the information about the barometric pressure and the information about the absolute pressure.

10. The method of claim 9, in which the communicating information comprises wirelessly communicating the information to the implantable medical device, wherein the implantable medical device is separate from and unattached to at least one of the first and second sensors.

11. The method of claim 9, comprising delivering therapy using the information about the gauge pressure as a control.

12. The method of claim 9, comprising trending over time the information about the gauge pressure.

13. The method of claim 9, in which the communicating includes one or more of acoustic communication, radio frequency communication, inductive communication, and communication using the body as an electrical signal conductor.

14. The method of claim 9, comprising anchoring at least a portion of a first sensor within the airway.

15. The method of claim 14, in which the anchoring comprises expanding an anchor.

16. The method of claim 15, comprising receiving or transmitting a communication signal using the anchor as an antenna.

17. A system comprising:
    an implantable medical device, including:
        a first sensor interface circuit,
        a second sensor interface circuit, and
        a biocompatible housing configured to include at least a portion of the first and second interface circuits;
    a first sensor module, at least a portion of which is adapted to reside within an airway of a subject's body, separate and remote from and unattached to the implantable medical device, wherein the first sensor module comprises:
        a first detector configured to detect external barometric pressure from within the airway; and a first communication module, coupled to the first detector, configured to transmit information about the barometric pressure to the first sensor interface circuit; and
an anchor, attached to the first sensor module, the anchor configured to fixate at least a portion of the first sensor module within the airway; and
a second sensor module, at least a portion of which is adapted to reside within a circulatory system of the body, separate and remote from and unattached to the implantable medical device and the first sensor module, wherein the second sensor module comprises:
a second detector configured to detect an absolute physiological pressure; and
a second communication module, coupled to the second detector, configured to transmit information about the absolute pressure to the second sensor interface circuit;

wherein the implantable medical device includes a processor configured to derive a gauge pressure using information about the absolute pressure received from the second detector and using barometric pressure information received from the first detector.

18. The system of claim 17, wherein the first sensor module comprises:
an energy storage device, coupled to at least the first detector and the first communication module; and
an anchor, configured to fixate at least a portion of the first detector within the airway.

19. The system of claim 18, wherein the second sensor module comprises:
an anchor configured to fixate at least a portion of the second detector within the circulatory system.

* * * * *

UNITED STATES PATENT AND TRADEMARK OFFICE
CERTIFICATE OF CORRECTION

PATENT NO.         : 7,744,542 B2                                    Page 1 of 1
APPLICATION NO.    : 11/379396
DATED              : June 29, 2010
INVENTOR(S)        : Thomas Piaget et al.

It is certified that error appears in the above-identified patent and that said Letters Patent is hereby corrected as shown below:

In column 11, line 10, in Claim 17, delete "implantable" and insert -- implantable --, therefor.

Signed and Sealed this

Seventeenth Day of August, 2010

David J. Kappos
*Director of the United States Patent and Trademark Office*